United States Patent
Schor

(10) Patent No.: US 11,191,603 B1
(45) Date of Patent: Dec. 7, 2021

(54) SURGICAL TOOL SUPPORT SYSTEM

(71) Applicant: Cynthia Schor, Miller Place, NY (US)

(72) Inventor: Cynthia Schor, Miller Place, NY (US)

( * ) Notice: Subject to any disclaimer, the term of this patent is extended or adjusted under 35 U.S.C. 154(b) by 0 days.

(21) Appl. No.: 17/196,114

(22) Filed: Mar. 9, 2021

(51) Int. Cl.
    *A61B 50/22* (2016.01)
    *A47B 81/00* (2006.01)

(52) U.S. Cl.
    CPC .............. *A61B 50/22* (2016.02); *A47B 81/00* (2013.01)

(58) Field of Classification Search
    CPC ... A61B 50/20; A61B 50/22; A47B 2097/003; A47B 81/005
    See application file for complete search history.

(56) References Cited

U.S. PATENT DOCUMENTS

| | | | | |
|---|---|---|---|---|
| 3,696,920 A | * | 10/1972 | Lahay | A61B 50/30 206/370 |
| 3,868,016 A | * | 2/1975 | Szpur | A61B 50/20 206/350 |
| 4,149,635 A | * | 4/1979 | Stevens | A61B 50/33 206/370 |
| 4,928,917 A | * | 5/1990 | Wolf | A61B 50/20 248/507 |
| 4,971,271 A | * | 11/1990 | Sularz | A61M 5/1418 248/229.13 |
| 5,046,624 A | | 9/1991 | Murphy | |
| D321,249 S | * | 10/1991 | Gorski | D24/229 |
| 5,137,151 A | * | 8/1992 | Choate | A61B 50/22 206/370 |
| 5,145,655 A | * | 9/1992 | Darlak | A61B 50/33 211/123 |
| 5,201,430 A | | 4/1993 | Artzer | |
| 5,307,924 A | * | 5/1994 | Manosalva | A61B 17/0401 206/339 |
| 5,312,250 A | * | 5/1994 | Ellman | A61C 19/02 433/77 |
| 5,407,069 A | * | 4/1995 | Schmieding | A61L 2/07 206/354 |
| 5,451,380 A | * | 9/1995 | Zinnanti | A61L 2/26 206/370 |

(Continued)

FOREIGN PATENT DOCUMENTS

| | | | | |
|---|---|---|---|---|
| DE | 29714090 U1 | * | 10/1997 | A61B 50/30 |
| DE | 19740843 C1 | * | 8/1998 | A61B 50/22 |

(Continued)

*Primary Examiner* — Stanton L Krycinski
(74) *Attorney, Agent, or Firm* — Kyle A. Fletcher, Esq.

(57) ABSTRACT

The surgical tool support system comprises a central tube, a left base, and a right base. The surgical tool support system may be an organizer for a plurality of surgical instruments. The central tube may be corrugated and expandable. When expanded, the central tube may expose a plurality of troughs disposed longitudinally along the central tube. Each of the plurality of troughs may support one or more surgical instruments. An individual surgical instrument may be placed on the surgical tool support system with a point of the individual surgical instrument down against a stand and a handle of the individual surgical instrument resting in one of the plurality of troughs. The surgical tool support system may replace a surgical instrument roll made from a towel, thus eliminating the time and complexity of forming the surgical instrument roll.

18 Claims, 5 Drawing Sheets

(56) References Cited

U.S. PATENT DOCUMENTS

| | | | | |
|---|---|---|---|---|
| 5,681,539 | A * | 10/1997 | Riley | A61L 2/26 206/370 |
| 6,244,447 | B1 * | 6/2001 | Frieze | A61L 2/07 206/370 |
| 6,367,637 | B1 | 4/2002 | Davis | |
| 6,561,352 | B2 * | 5/2003 | Sherman | A61M 5/3205 206/366 |
| 6,629,615 | B2 * | 10/2003 | Kim | F16L 3/223 211/85.13 |
| D482,197 | S | 11/2003 | Vazquez | |
| 7,303,568 | B2 | 12/2007 | Jannot | |
| 7,871,581 | B1 * | 1/2011 | Coleman | A61L 2/26 422/300 |
| 8,069,998 | B2 * | 12/2011 | Thomas | A61B 50/30 211/85.13 |
| 8,162,156 | B1 | 4/2012 | Crisman | |
| 8,505,748 | B2 * | 8/2013 | Jones | A61B 50/22 211/85.13 |
| 8,511,468 | B2 * | 8/2013 | Reeves | A61B 50/20 206/370 |
| 8,523,824 | B2 * | 9/2013 | Teirstein | A61M 25/02 604/174 |
| 9,060,913 | B2 * | 6/2015 | Hensler | A61G 7/0518 |
| 9,115,948 | B2 * | 8/2015 | Murphey | F41C 33/007 |
| 9,444,237 | B2 * | 9/2016 | Frojo | H02G 3/30 |
| 9,782,231 | B2 * | 10/2017 | Freerks | A61B 50/20 |
| 9,833,529 | B2 * | 12/2017 | Tipton | A61B 50/20 |
| 9,863,556 | B2 * | 1/2018 | Robert, Jr. | F16L 3/10 |
| 10,016,239 | B2 | 7/2018 | Reeves | |
| 10,271,918 | B2 * | 4/2019 | Chow | A61M 25/02 |
| 10,391,190 | B1 * | 8/2019 | Oko | A61L 2/07 |
| 11,033,711 | B2 * | 6/2021 | Coatsworth | A61B 50/20 |
| 2004/0073233 | A1 * | 4/2004 | Jannot | A61B 17/06061 606/148 |
| 2004/0206711 | A1 * | 10/2004 | Hoftman | A61B 50/22 211/85.13 |
| 2004/0222175 | A1 * | 11/2004 | Keating | A61B 50/20 211/85.13 |
| 2005/0061696 | A1 * | 3/2005 | Swank | A61B 50/20 206/363 |
| 2006/0037920 | A1 * | 2/2006 | Baranya | A47L 13/512 211/70.6 |
| 2006/0076254 | A1 | 4/2006 | Corbitt | |
| 2008/0011699 | A1 | 12/2008 | Lyons | |
| 2009/0184225 | A1 * | 7/2009 | Gleick | A63B 71/0036 248/314 |
| 2016/0066997 | A1 * | 3/2016 | Ren | A61B 50/20 211/85.13 |
| 2016/0089204 | A1 * | 3/2016 | Chow | A61M 25/02 224/217 |
| 2019/0246793 | A1 * | 8/2019 | Weikert | A61B 17/00 |
| 2019/0376621 | A1 * | 12/2019 | Cattaneo | H02G 11/006 |
| 2021/0031001 | A1 * | 2/2021 | Coatsworth | A61M 25/002 |

FOREIGN PATENT DOCUMENTS

| | | | | |
|---|---|---|---|---|
| DE | 102006029061 A1 * | 1/2008 | | A61B 50/20 |
| EP | 0437192 A1 * | 7/1991 | | A61B 50/37 |
| GB | 991431 A * | 5/1965 | | F16L 3/223 |
| WO | 2001064082 | 9/2001 | | |
| WO | WO-2011029017 A1 * | 3/2011 | | A61B 50/20 |

\* cited by examiner

SURGICAL TOOL SUPPORT SYSTEM

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of surgical equipment, more specifically, a surgical tool support system.

SUMMARY OF INVENTION

The surgical tool support system comprises a central tube, a left base, and a right base. The surgical tool support system may be an organizer for a plurality of surgical instruments. The central tube may be corrugated and expandable. When expanded, the central tube may expose a plurality of troughs disposed longitudinally along the central tube. Each of the plurality of troughs may support one or more surgical instruments. An individual surgical instrument may be placed on the surgical tool support system with a point of the individual surgical instrument down against a stand and a handle of the individual surgical instrument resting in one of the plurality of troughs. The surgical tool support system may replace a surgical instrument roll made from a towel, thus eliminating the time and complexity of forming the surgical instrument roll.

An object of the invention is to organize surgical instruments.

Another object of the invention is to provide a corrugated central tube that may be expanded and compressed by manipulating a left base and a right base coupled to the ends of the central tube.

A further object of the invention is to provide a plurality of troughs on the expanded central tube for supporting the surgical instruments.

Yet another object of the invention is to provide coplanar flat side on the left base and the right base such that the surgical tool support system remains stationary while in use.

These together with additional objects, features and advantages of the surgical tool support system will be readily apparent to those of ordinary skill in the art upon reading the following detailed description of the presently preferred, but nonetheless illustrative, embodiments when taken in conjunction with the accompanying drawings. In this respect, before explaining the current embodiments of the surgical tool support system in detail, it is to be understood that the surgical tool support system is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the surgical tool support system.

It is therefore important that the claims be regarded as including such equivalent construction insofar as they do not depart from the spirit and scope of the surgical tool support system. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description. As used herein, the word "or" is intended to be inclusive.

Figure 1:
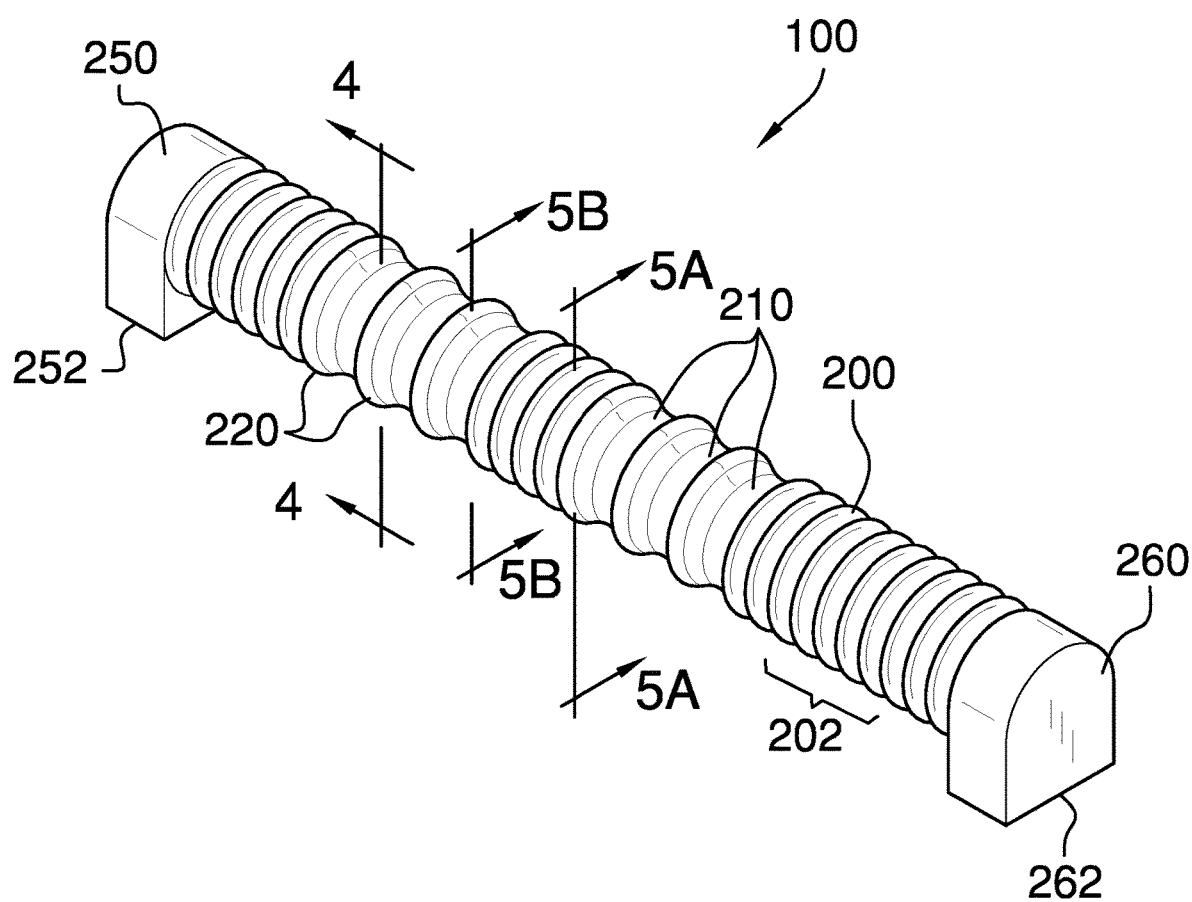
FIG. 1 is an isometric view of an embodiment of the disclosure.
Figure 2:
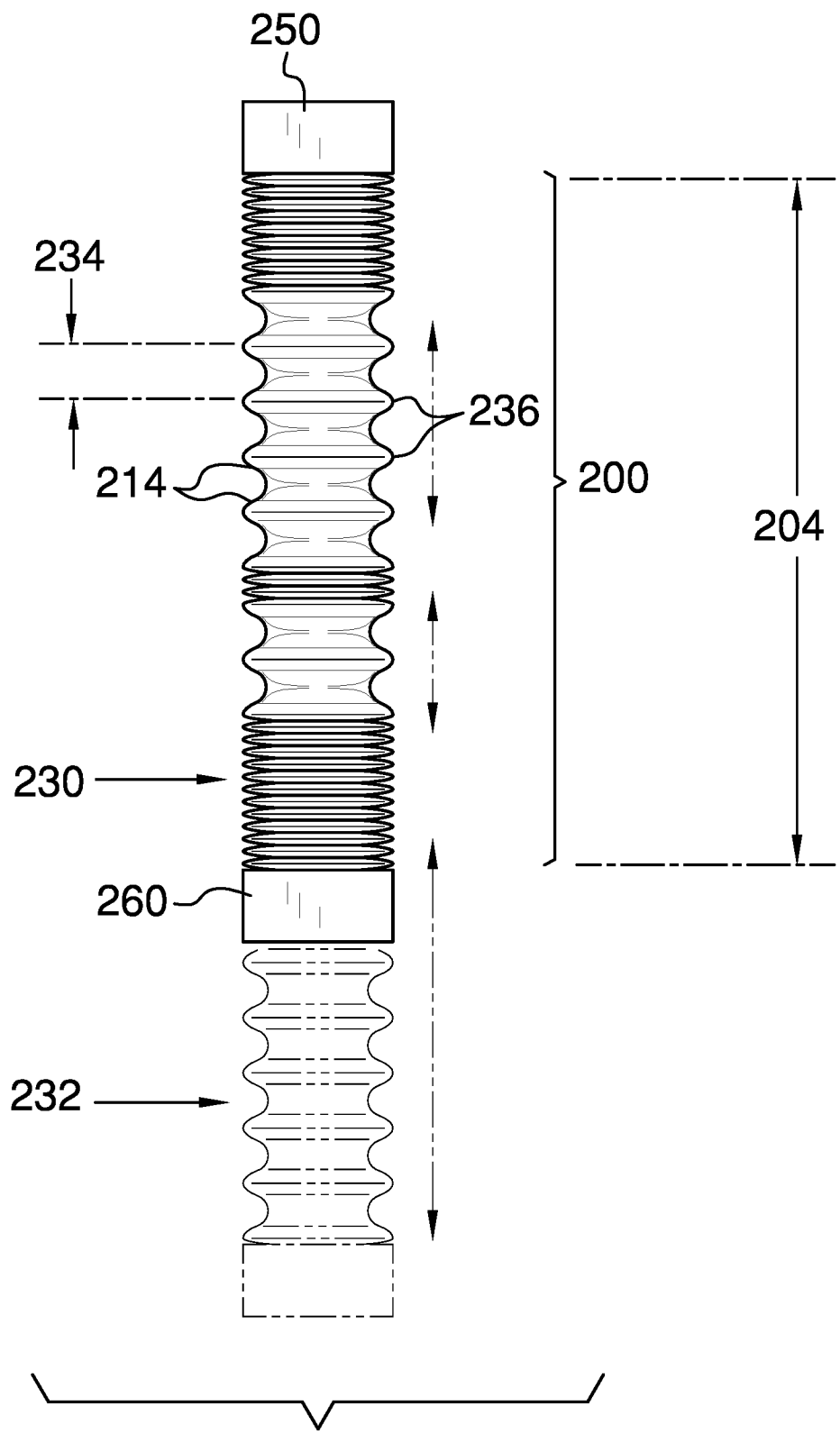
FIG. 2 is a bottom view of an embodiment of the disclosure.
Figure 3:
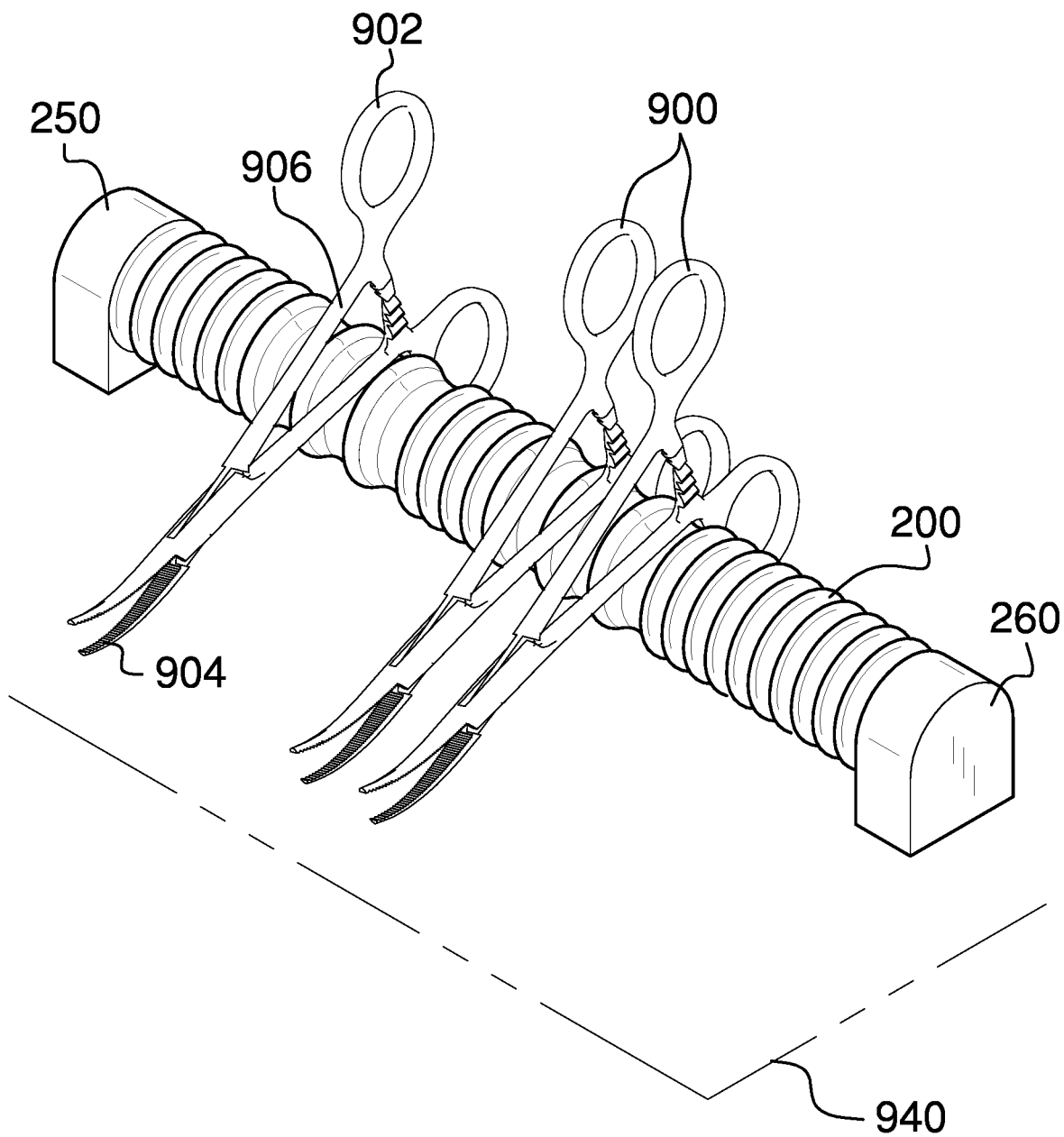
FIG. 3 is an in-use view of an embodiment of the disclosure.
Figure 4:
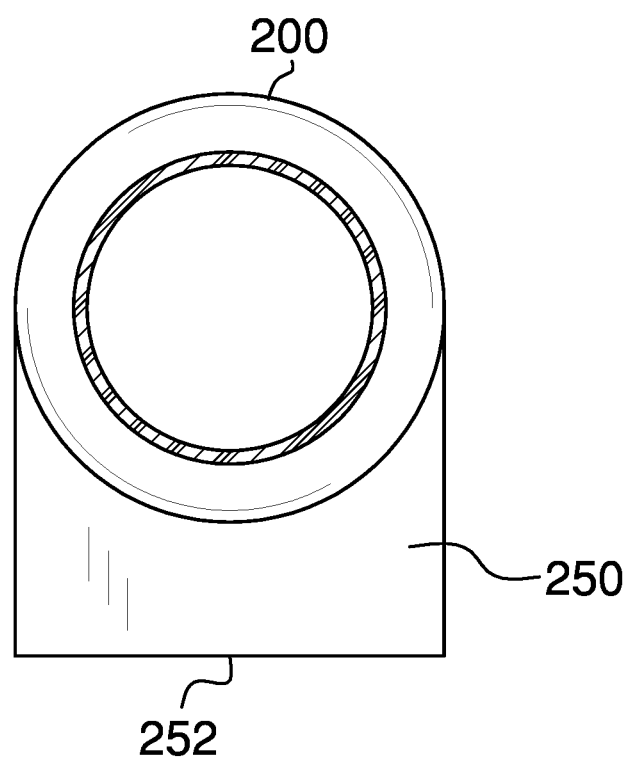
FIG. 4 is a cross-sectional view of an embodiment of the disclosure across 4-4 as shown in FIG. 1.
Figure 5:
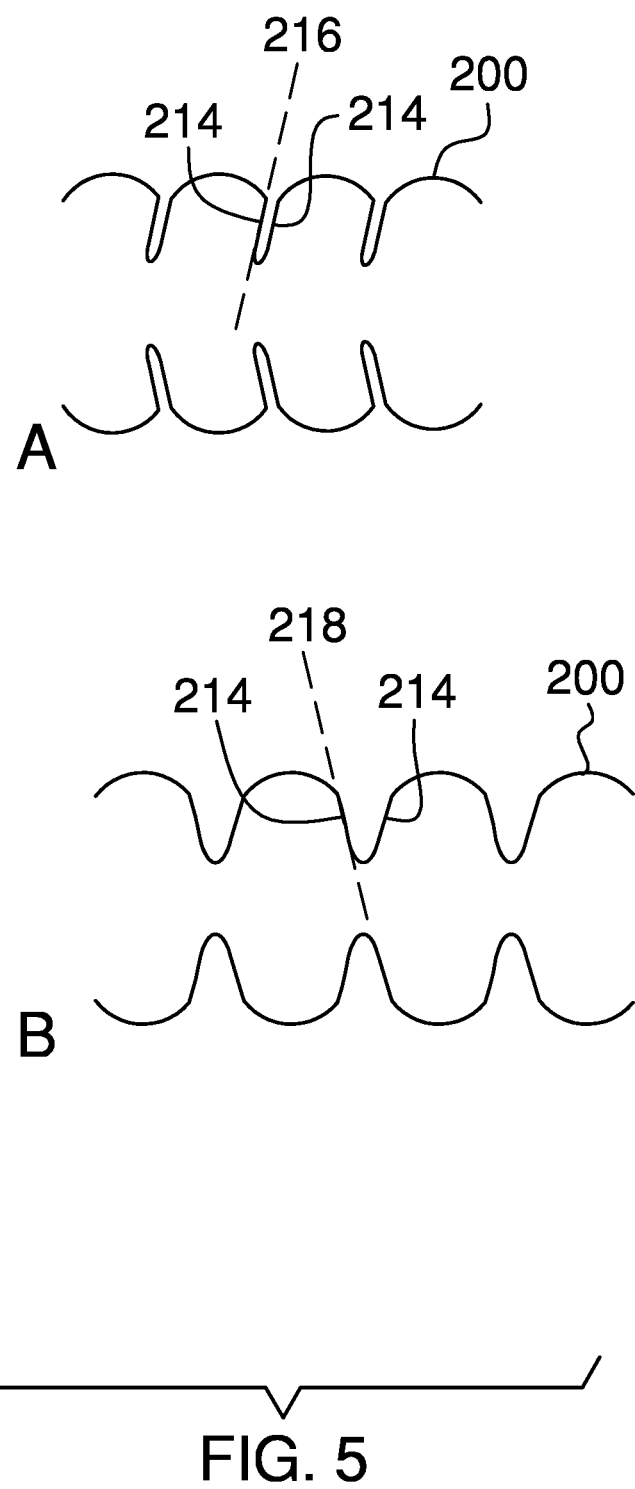
FIG. 5A is a cross-sectional view of an embodiment of the disclosure across 5A-5A as shown in FIG. 1, illustrating a side wall in a first bistable position.
FIG. 5B is a cross-sectional view of an embodiment of the disclosure across 5B-5B as shown in FIG. 1, illustrating a side wall in a second bistable position.

Detailed reference will now be made to a first potential embodiment of the disclosure, which is illustrated in FIGS. 1 through 5B.

The surgical tool support system 100 (hereinafter invention) comprises a central tube 200, a left base 250, and a right base 260. The invention 100 may be an organizer for a plurality of surgical instruments 900. The central tube 200 may be corrugated and expandable. When expanded, the central tube 200 may expose a plurality of troughs 210 disposed longitudinally along the central tube 200. Each of the plurality of troughs 210 may support one or more surgical instruments. An individual surgical instrument 902 selected from the plurality of surgical instruments 900 may be placed on the invention 100 with a point 904 of the individual surgical instrument 902 down against a stand 940 and a handle 906 of the individual surgical instrument 902 resting in one of the plurality of troughs 210. As non-limiting examples, the plurality of surgical instruments 900 may be scissors, hemostats, clamps, or combinations thereof. The invention 100 may replace a surgical instrument roll which may be a towel that has been rolled and pleated to provide support for the plurality of surgical instruments 900, thus eliminating the time and complexity of forming the surgical instrument roll.

The central tube 200 may comprise corrugations 202 disposed along the central tube 200 longitudinally. A longitudinal length 204 of the central tube 200 may be changed due to flexibility inherent in the corrugations 202. The corrugations 202 may comprise the plurality of troughs 210 and a plurality of ridges 220. An individual trough selected from the plurality of troughs 210 may be a circumferential narrowing of the diameter of the central tube 200.

An individual ridge selected from the plurality of ridges 220 may be a circumferential thickening of the central tube 200 between two of the individual troughs. The diameter of the central tube 200 at the individual ridge may be thought of as the actual diameter of the central tube 200 and the plurality of troughs 210 may be considered to be constrictions of the central tube 200.

The individual trough may be coupled to the individual ridges on either side of the individual trough via side walls 214. The side walls 214 may be semirigid and may be moved to one of two bistable positions. In a first bistable position 216, the side walls 214 may pull the individual ridges on either side of the individual trough together such that the individual ridges on either side of the individual trough are adjacent and the individual trough is not exposed. In a second bistable position 218, the side walls 214 may push the individual ridges on either side of the individual trough apart such that the individual ridges on either side of the individual trough separate and the individual trough is exposed.

The central tube 200 may be expandable such that the longitudinal length 204 of the central tube 200 may increase when the central tube 200 is stretched longitudinally and may decrease when the central tube 200 is compressed from the ends. The central tube 200 may be maximally expanded by stretching the central tube 200 longitudinally such that all of the plurality of troughs 210 become exposed. The central tube 200 may be partially expanded by stretching the central tube 200 longitudinally such that a subset of the plurality of troughs 210 become exposed. The central tube 200 may be said to be in a compressed state 230 when none of the plurality of troughs 210 are exposed. The central tube 200 may be said to be in an expanded state 232 when at last one of the plurality of troughs 210 are exposed.

A pitch 234 may be the longitudinal distance between the crests of adjacent ridges 236. The pitch 234 may change based upon whether the central tube 200 is in the compressed state 230 or in the expanded state 232. A compressed pitch may be the distance between the adjacent ridges 236 when the adjacent ridges 236 are adjacent to each other and the individual trough located between the adjacent ridges 236 is not exposed. An expanded pitch may be the distance between the adjacent ridges 236 when the adjacent ridges 236 are separated and the individual trough located between the adjacent ridges 236 is exposed. The expanded pitch may be at least twice the compressed pitch.

In a preferred embodiment, the longitudinal length 204 of the central tube 200 may be 6 inches+/−2 inches when fully compressed and 18 inches+/−2 inches when fully expanded.

The central tube 200 may be made from medical grade polymers. As non-limiting examples, the central tube 200 may be made from PTFE (polytetrafluoroethylene), FEP (fluorinated ethylene propylene), EVA (ethylene vinyl acetate), PE (polyethylene), PP (polypropylene), silicone, or combinations thereof.

The central tube 200 may be coupled on a left end to the left base 250 and on a right end to the right base 260. The left base 250 and the right base 260 may be support blocks that hold the central tube 200 in place and in the expanded state 232 during use. As least one lateral side of the left base 250 may be a flat left side 252 to prevent the left base 250 from rolling. As least one lateral side of the right base 260 may be a flat right side 262 to prevent the right base 260 from rolling. The flat left side 252 and the flat right side 262 may be coplanar. The distance from the flat left side 252 to the center of the left base 250 and from the flat right side 262 to the center of the right base 260 may be larger than the radius of the central tube 200 such that the flat left side 252 and the flat right side 262 contact the stand 940 to prevent rolling.

The invention 100 may be sterilized before use to prevent contamination of the plurality of surgical instruments 900. As non-limiting examples, the invention 100 may be sterilized by exposure to UV light, chemicals, heat, radiation, or combinations thereof. In some embodiments, the invention 100 may be hermetically sealed while sterile such that the invention 100 may be removed from packaging and used In use, a surgical technician may prepare for a medical procedure by removing the invention 100 from sterile packaging (if any) and by placing the invention 100 on the stand 940. The central tube 200 may be stretched to expose some or all of the plurality of troughs 210 by grasping the left base 250 and the right base 260 and pulling them away from each other. The plurality of surgical instruments 900 may be placed on the central tube 200 such that the point 904 of each of the individual surgical instruments 902 rests on the stand 940 and the handle 906 of the individual surgical instrument 902 rests in one of the individual troughs of the central tube 200. When multiple types of instruments are placed upon the central tube 200 at the same time it is considered good practice to group one or more surgical instruments of the same type together so that the individual surgical instruments 902 of a specific type may be found quickly. In some embodiments, the invention 100 may be disposed on after use. In some embodiments, the invention 100 may be cleaned and sterilized after use and may be re-used.

DEFINITIONS

Unless otherwise stated, the words "up", "down", "top", "bottom", "upper", and "lower" should be interpreted within a gravitational framework. "Down" is the direction that gravity would pull an object. "Up" is the opposite of "down". "Bottom" is the part of an object that is down farther than any other part of the object. "Top" is the part of an object that is up farther than any other part of the object. "Upper" may refer to top and "lower" may refer to the bottom. As a non-limiting example, the upper end of a vertical shaft is the top end of the vertical shaft.

As used herein, the words "couple", "couples", "coupled" or "coupling", may refer to connecting, either directly or indirectly, and does not necessarily imply a mechanical connection.

As used in this disclosure, a "diameter" of an object is a straight line segment that passes through the center (or center axis) of an object. The line segment of the diameter is terminated at the perimeter or boundary of the object through which the line segment of the diameter runs.

As used herein, "handle" may refer to an object by which a tool, object, or door is held or manipulated with the hand.

As used herein, "hermetically sealed" may refer to an airtight, and therefore watertight, barrier or enclosure.

As used in this disclosure, the word "lateral" may refer to the sides of an object or movement towards a side. Lateral directions are generally perpendicular to longitudinal directions. "Laterally" may refer to movement in a lateral direction.

As used herein, the word "longitudinal" or "longitudinally" may refer to a lengthwise or longest direction.

As used herein, "resilient" or "semi-rigid" may refer to an object or material which will deform when a force is applied to it and which will return to its original shape when the deforming force is removed.

As used in this disclosure, "UV" may be an abbreviation for ultraviolet.

With respect to the above description, it is to be realized that the optimum dimensional relationship for the various components of the invention described above and in FIGS. 1 through 5B, include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

The inventor claims:

1. A surgical tool support system comprising:
a central tube, a left base, and a right base;
wherein the surgical tool support system is an organizer for a plurality of surgical instruments;
wherein the central tube is corrugated and expandable;
wherein when expanded, the central tube exposes a plurality of troughs disposed longitudinally along the central tube;
wherein each of the plurality of troughs support one or more of the plurality of surgical instruments;
wherein the central tube comprises corrugations disposed along the central tube longitudinally;
wherein an individual surgical instrument selected from the plurality of surgical instruments is placed on the surgical tool support system with a point of the individual surgical instrument down against a stand and a handle of the individual surgical instrument resting in one of the plurality of troughs;
wherein a longitudinal length of the central tube changes due to flexibility inherent in the corrugations.

2. The surgical tool support system according to claim 1 wherein the corrugations comprise the plurality of troughs and a plurality of ridges;
wherein an individual troughs selected from the plurality of troughs are each a circumferential narrowing of the diameter of the central tube.

3. The surgical tool support system according to claim 2 wherein individual ridges selected from the plurality of ridges are each a circumferential thickening of the central tube between two of the individual troughs.

4. The surgical tool support system according to claim 3 wherein a respective one of the individual troughs is coupled to a respective individual ridges of the individual ridges on either side of the individual trough via side walls;
wherein the side walls are semirigid and are movable to one of two bistable positions.

5. The surgical tool support system according to claim 4 wherein in a first bistable position, the side walls pull the individual ridges on either side of the individual trough together such that the individual ridges on either side of the individual trough are adjacent and the individual trough is not exposed;
wherein in a second bistable position, the side walls push the individual ridges on either side of the individual trough apart such that the individual ridges on either side of the individual trough separate and the individual trough is exposed.

6. The surgical tool support system according to claim 5 wherein the central tube is expandable such that the longitudinal length of the central tube increases when the central tube is stretched longitudinally and decreases when the central tube is compressed from ends of the central tube.

7. The surgical tool support system according to claim 6 wherein the central tube is maximally expanded by stretching the central tube longitudinally such that all of the plurality of troughs become exposed.

8. The surgical tool support system according to claim 7 wherein the central tube is partially expanded by stretching the central tube longitudinally such that a subset of the plurality of troughs become exposed.

9. The surgical tool support system according to claim 8 wherein the central tube is in a compressed state when none of the plurality of troughs are exposed;
wherein the central tube is in an expanded state when at last one of the plurality of troughs are exposed.

10. The surgical tool support system according to claim 9 wherein a pitch is the longitudinal distance between the crests of adjacent ridges of the plurality of ridges;
wherein the pitch changes based upon whether the central tube is in the compressed state or in the expanded state;
wherein a compressed pitch is the distance between the adjacent ridges when the adjacent ridges are adjacent to each other and the individual trough located between the adjacent ridges is not exposed;
wherein an expanded pitch is the distance between the adjacent ridges when the adjacent ridges are separated and the individual trough located between the adjacent ridges is exposed.

11. The surgical tool support system according to claim 10 wherein the expanded pitch is at least twice the compressed pitch.

12. The surgical tool support system according to claim 10 wherein the longitudinal length of the central tube is 4 to 8 inches when fully compressed and 16 to 20 inches when fully expanded.

13. The surgical tool support system according to claim 10 wherein the central tube is coupled on a left end to the left base and on a right end to the right base;

wherein the left base and the right base are support blocks that hold the central tube in place and in the expanded state during use.

14. The surgical tool support system according to claim 13
wherein as least one lateral side of the left base is a flat left side to prevent the left base from rolling;
wherein as least one lateral side of the right base is a flat right side to prevent the right base from rolling.

15. The surgical tool support system according to claim 14
wherein the flat left side and the flat right side are coplanar.

16. The surgical tool support system according to claim 15
wherein the distance from the flat left side to the center of the left base and from the flat right side to the center of the right base are larger than the radius of the central tube such that the flat left side and the flat right side contact the stand to prevent rolling.

17. The surgical tool support system according to claim 16
wherein the surgical tool support system is sterilized before use to prevent contamination of the plurality of surgical instruments.

18. The surgical tool support system according to claim 17
wherein the surgical tool support system is hermetically sealed while sterile;
wherein the surgical tool support system is removable from packaging and usable while sterile.

* * * * *